US008529546B2

(12) United States Patent
Alvarez (10) Patent No.: US 8,529,546 B2
(45) Date of Patent: Sep. 10, 2013

(54) SINUSAL GUIDE CANNULA AND KIT FOR IRRIGATION, SUCTION AND WASHING

(75) Inventor: William De Jesus Alvarez, Antioquia (CO)

(73) Assignee: John J. Martinez, Croton on Hudson, NY (US)

( * ) Notice: Subject to any disclaimer, the term of this patent is extended or adjusted under 35 U.S.C. 154(b) by 0 days.

(21) Appl. No.: 12/909,812

(22) Filed: Oct. 21, 2010

(65) Prior Publication Data
US 2012/0101433 A1   Apr. 26, 2012

(51) Int. Cl.
*A61M 1/00*   (2006.01)
(52) U.S. Cl.
USPC ............................. 604/540; 604/73; 604/187
(58) Field of Classification Search
USPC ................. 604/73, 96.01, 187, 514, 516, 540, 604/544
See application file for complete search history.

(56) References Cited

U.S. PATENT DOCUMENTS

| 1,879,249 A * | 9/1932 | Honsaker ........................ 604/27 |
| 5,084,016 A * | 1/1992 | Freeman et al. .............. 604/103 |
| 5,129,889 A * | 7/1992 | Hahn et al. .................... 604/265 |
| 5,509,909 A * | 4/1996 | Moy ............................. 604/540 |
| 7,195,614 B2 * | 3/2007 | Geisler et al. ............ 604/170.01 |

* cited by examiner

*Primary Examiner* — Laura Bouchelle
(74) *Attorney, Agent, or Firm* — Martinez Patents P.C.; John J. Martinez (57) ABSTRACT

The present invention provides a cannula guide tube; and a kit with the cannula guide tube, a flexible transparent cannula or a transparent catheter with an inflatable balloon at the catheter end, and an exploratory device. The kit is for irrigation, suction and washing out purulent or liquid discharges from bacteria infected sinuses. First, the exploratory device is used to find the entrance orifice to a sinus; second, the cannula guide tube is positioned in the sinus orifice entrance; and third, the flexible transparent cannula or the transparent catheter is inserted through the cannula guide tube into the sinus. The flexible transparent cannula or transparent catheter is used to suction the purulent or liquid discharge and to irrigate and wash out the sinus. The cannula guide tube has an opening before the tube end, wherein the opening allows seeing the flexible transparent cannula or transparent catheter inside the tube and the flow of purulent or liquid discharge suctioned from the sinus, as the purulent discharge flows throughout the flexible transparent cannula or the transparent catheter.

10 Claims, 9 Drawing Sheets

SINUSAL GUIDE CANNULA AND KIT FOR IRRIGATION, SUCTION AND WASHING

BACKGROUND OF THE INVENTION

1. Field of the Invention

The present invention is related to a guide for a sinusal cannula (canula), and a kit that comprises the guide, a cannula and an exploratory tubular device, for irrigation, suction and washing out purulent discharges from infected sinus.

2. Description of Prior Art

Infected sinus or sinusitis is a very common malady in humans or animals, wherein sinuses, e.g., maxillary sinuses, frontal sinuses, etc., get infected with bacteria, resulting in accumulation of purulent discharges within the sinuses. In addition to treatment with antibacterial antibiotics, the purulent discharges must be drained or washed out by irrigation with, for example, saline solution. If the purulent discharges are not drained out from the sinuses, treatment with antibiotics fails, and spreading of the bacteria to neighboring organs, e.g., brain, may occur.

Prior art medical procedures for irrigation, suction and washing out sinuses of purulent discharges are hard to carry out because of inflammation which makes difficult locating an infected sinus entrance. This limitation causes surgeons to break sinuses neighboring bones in order to gain access and drain purulent and liquid discharges. Another way of draining out purulent and liquid discharges from infected sinuses makes use of a balloon to dilate the infected sinus entrance. However, in this later method, because there is no instant monitoring of whether the purulent discharge or liquid is flowing out of the infected sinus, surgeons sometimes manipulate unnecessarily or try several times to locate the sinus entrance to assure that the balloon is placed adequately. In addition, during irrigation of sinuses, it is also difficult to see, when purulent discharges are completely coming out, as the purulent discharge flow is replaced by clear irrigation fluid flow.

The present invention overcomes the limitations of prior art medical methods for irrigation, suction and washing sinuses. The present invention provides a way to easily locate an infected sinus entrance, to place a device which allows instant monitoring of what is coming out from the infected sinuses, when said infected sinuses are irrigated, suctioned or washed out, with minimum trauma to the sinus inflamed surrounding tissues.

SUMMARY OF THE INVENTION

The present invention provides a cannula guide tube; and a kit with the cannula guide tube, a flexible transparent cannula or a transparent catheter with an inflatable balloon at the catheter end, and an exploratory device. The kit is for irrigation, suction and washing out purulent or liquid discharges from bacteria infected sinuses. First, the exploratory device is used to find the entrance orifice to a sinus; second, the cannula guide tube is positioned in the sinus orifice entrance; and third, the flexible transparent cannula or the transparent catheter is inserted through the cannula guide tube into the sinus. The flexible transparent cannula or transparent catheter is used to suction the purulent or liquid discharge and to irrigate and wash out the sinus. The cannula guide tube has an opening before the tube end, wherein the opening allows seeing the flexible transparent cannula or transparent catheter inside the tube and the flow of purulent or liquid discharge suctioned from the sinus, as the purulent discharge flows throughout the flexible transparent cannula or the transparent catheter.

Specifically, the present invention provides a cannula guide for irrigation, suction and washing out purulent discharges or liquids from a sinus, wherein the cannula guide comprises a tube with a beginning and an end, wherein the tube has an opening on the tube portion preceding the end; wherein the cannula guide is used to conduct a flexible transparent cannula to a sinus cavity, wherein the flexible transparent cannula is used for irrigation, suction and washing out purulent discharges from the sinus cavity, wherein the opening allows to see the purulent discharge flow that is getting out from the sinus cavity, wherein the opening also allows to see a clean washing fluid flow after the purulent discharge is clear out of the sinus cavity.

In one aspect of the present invention, the cannula guide tube end forms an angle with respect to the rest of the tube, wherein the opening is inside of the angle just before the tube end.

In another aspect of the present invention, the cannula guide tube end has a non-sharp rounded olive shape.

In one more aspect of the present invention, the cannula guide tube beginning has a thickened pear like shape.

In an additional aspect of the present invention, the cannula guide tube has attached a coin shaped disk for gripping.

In a further aspect of the present invention, the cannula guide tube middle portion has a bend.

The present invention also provides a kit for irrigation, suction and washing out purulent sinusitis discharges, wherein the kit comprises:

A. a cannula guide tube with a beginning and an end, wherein the tube has an opening on the tube portion preceding the end; wherein the cannula guide tube is used to conduct a flexible transparent cannula to a sinus cavity, wherein the flexible transparent cannula is used for irrigation, suction and washing out purulent discharges from the sinus cavity, wherein the opening allows to see the purulent discharge flow that is getting out from the sinus cavity, wherein the opening also allows to see a clean washing fluid flow after the purulent discharge is clear out of the sinus cavity;

B. A flexible transparent cannula;

C. An exploratory tubular device that has first portion, a second portion and a third portion, wherein the first portion serves as the device holder, wherein the first portion is the thickest portion, wherein the second portion is the second uniformly thickest portion, wherein the third portion is the least thick portion, wherein the third portion termination is non-sharp.

In one aspect of the kit of the present invention, the cannula guide tube end forms an angle with respect to the rest of the tube, wherein the opening is inside of the angle just before the tube end.

In another aspect of the kit of the present invention, the cannula guide tube end has a non-sharp rounded olive shape.

In one more aspect of the kit of the present invention, the cannula guide tube beginning has a thickened pear like shape.

In an additional aspect of the kit of the present invention, the cannula guide tube has attached a coin shaped disk for gripping.

In a further aspect of the kit of the present invention, the cannula guide tube middle portion has a bend.

In an added aspect of the kit of the present invention, the tubular device second portion has a bend.

In one extra aspect of the kit of the present invention, the tubular device third portion termination forms an angle with respect to the rest of the tubular device.

In one more aspect of the kit of the present invention, the tubular device third portion termination has a non-sharp olive shape.

Additional objectives and advantages of the present invention will be more evident in the detailed description of the invention and the claims.

DETAILED DESCRIPTION OF THE INVENTION

Figure 1:
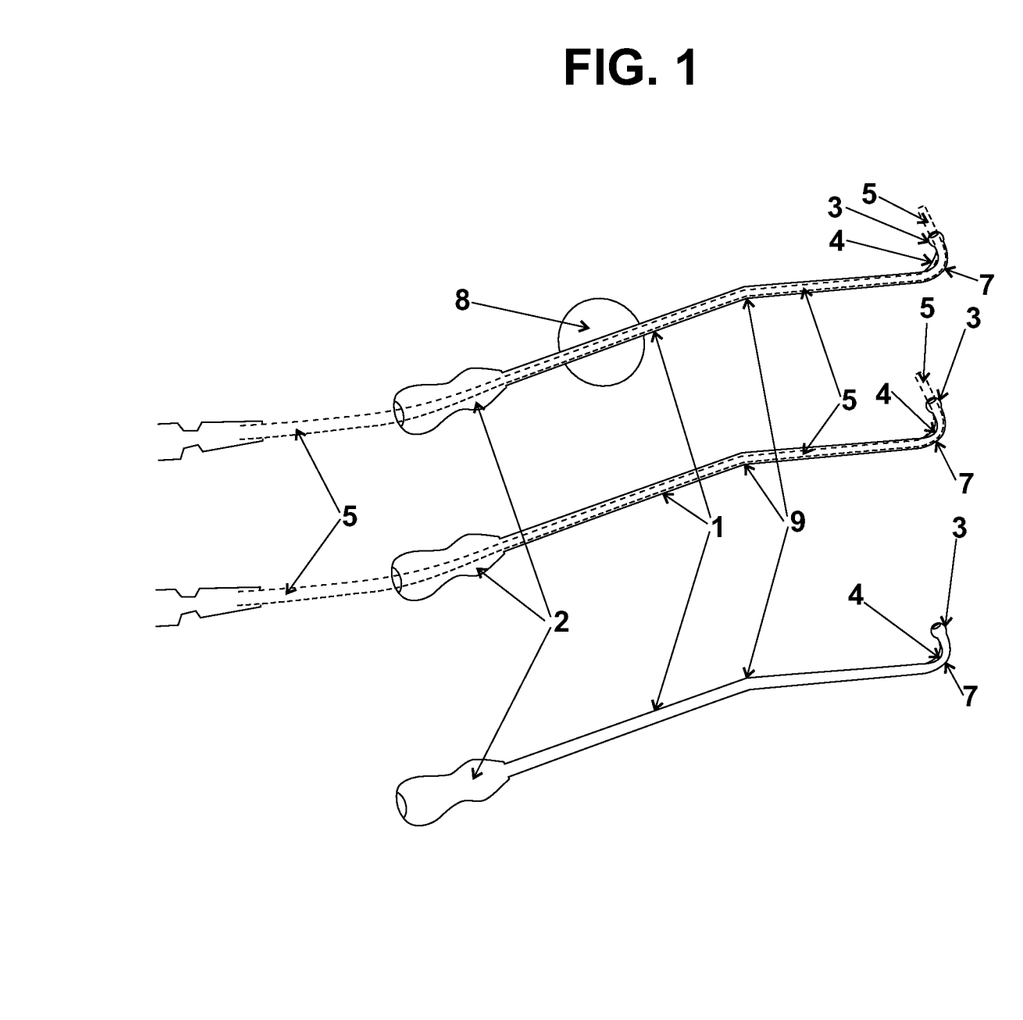
FIG. 1. Shows two embodiments of the cannula guide tube of the present invention, wherein the tube has inside a flexible transparent cannula. This figure also shows an embodiment of the cannula guide tube of the present invention without the flexible transparent cannula inside.

FIG. 1 shows two embodiments of a cannula guide for irrigation, suction and washing out purulent or liquid discharges from a sinus. The cannula guide comprises a tube (FIGS. 1-4) (1) with a beginning (FIGS. 1-4) (2) and an end (FIGS. 1-4) (3), wherein the tube has an opening (FIGS. 1-5) (4) on the tube portion preceding the end (3); wherein the cannula guide tube (1) is used to conduct a flexible transparent cannula (FIGS. 1-5) (5), or a transparent catheter with an inflatable balloon, to a sinus cavity (FIG. 3) (6), wherein the flexible transparent cannula (5) or the transparent catheter is used for irrigation, suction and washing out purulent discharges or liquids from the sinus cavity, wherein the opening (4) allows to see the purulent discharge or the liquid flow that is getting out from the sinus cavity, wherein the opening (4) also allows to see a clean washing fluid flow after the purulent discharge or liquid is clear out of the sinus cavity.

In a preferred use of the cannula guide tube (1) of the present invention, the cannula guide tube (1) is used to drain out purulent discharges or liquids from human sinuses, e.g., maxillary sinuses. However, the cannula guide tube (1) of the present invention can be also used to drain out discharges or liquids from animal sinuses.

In addition, the cannula guide tube (1) of the present invention can serve to irrigate other human or animal ducts, e.g., lachrymal ducts, wherein irrigating would clear blockages of said ducts.

In one preferred aspect of the present invention, the cannula guide tube end (3) forms an angle (FIGS. 1 to 5) (7) with respect to the rest of the tube, wherein the opening (4) is inside of the angle (7) just before the tube end (3). However, there may be situations wherein the angle before the end is not necessary.

In another preferred aspect of the present invention, the cannula guide tube end (3) has a non-sharp rounded olive shape (3 in FIGS. 1 to 5). However, the cannula guide tube end not necessarily has to have a olive shape finish, as long as, the cannula guide tube end does not have sharp borders that could damage soft tissues or inflammated tissues.

The cannula guide tube of the present invention preferably is made of stainless steel which will allow sterilization and reusing said cannula guide tube. However, the cannula guide tube of the present invention can also be made of any inert hard material, e.g., hard plastic, even if it is not reusable.

In one more aspect of the present invention, the cannula guide tube beginning (2) has a thickened pear like shape (2 in FIGS. 1 to 4).

In another embodiment of the present invention, the cannula guide tube (1) has attached a coin shaped disk (FIGS. 1 to 4) (8) for gripping.

Figure 2:
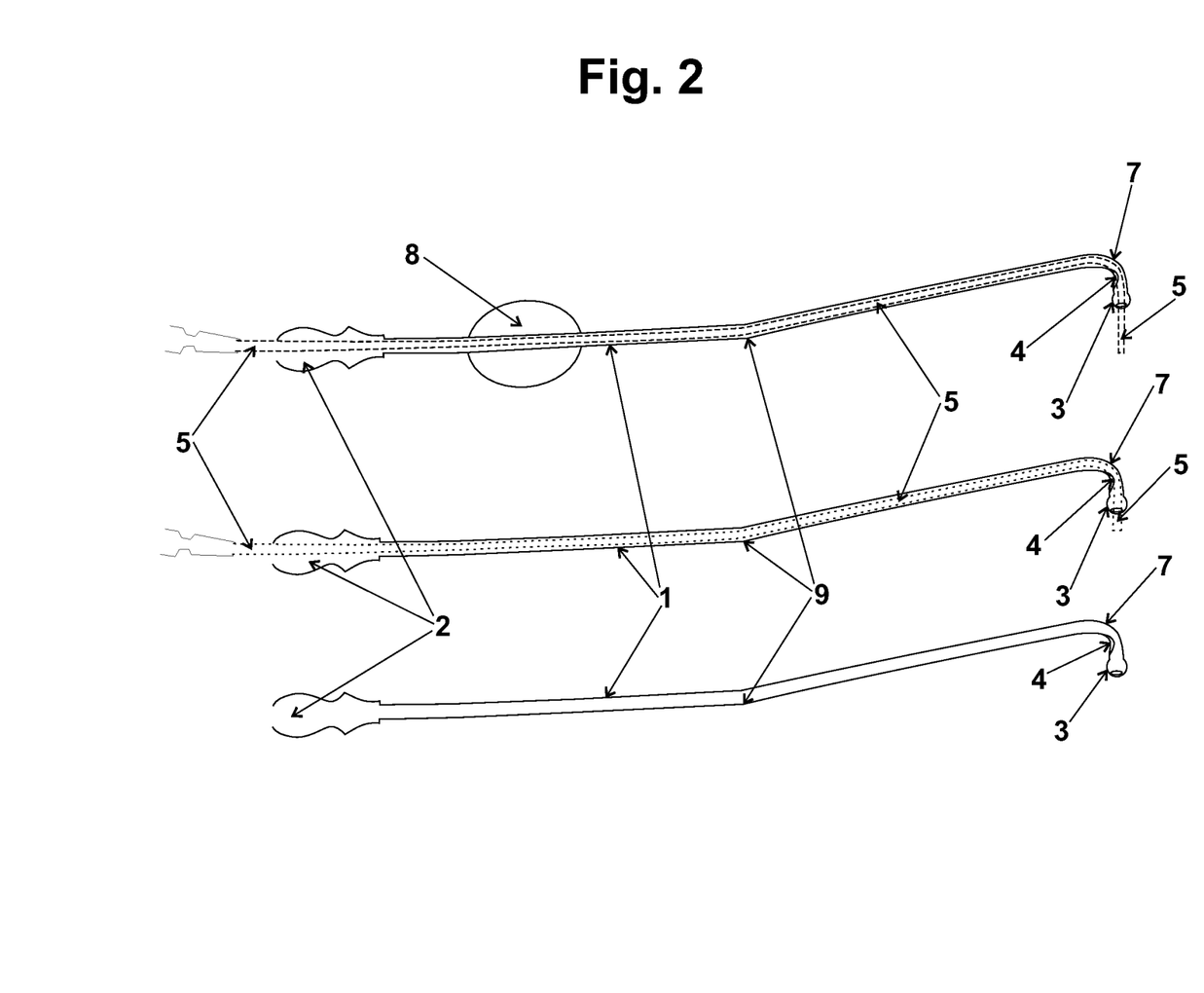
FIG. 2. Shows another view of two embodiments of the cannula guide tube of the present invention, wherein a tube has inside the flexible transparent cannula. This figure also shows another view of an embodiment of the cannula guide tube of the present invention without the flexible transparent cannula inside.
Figure 3:
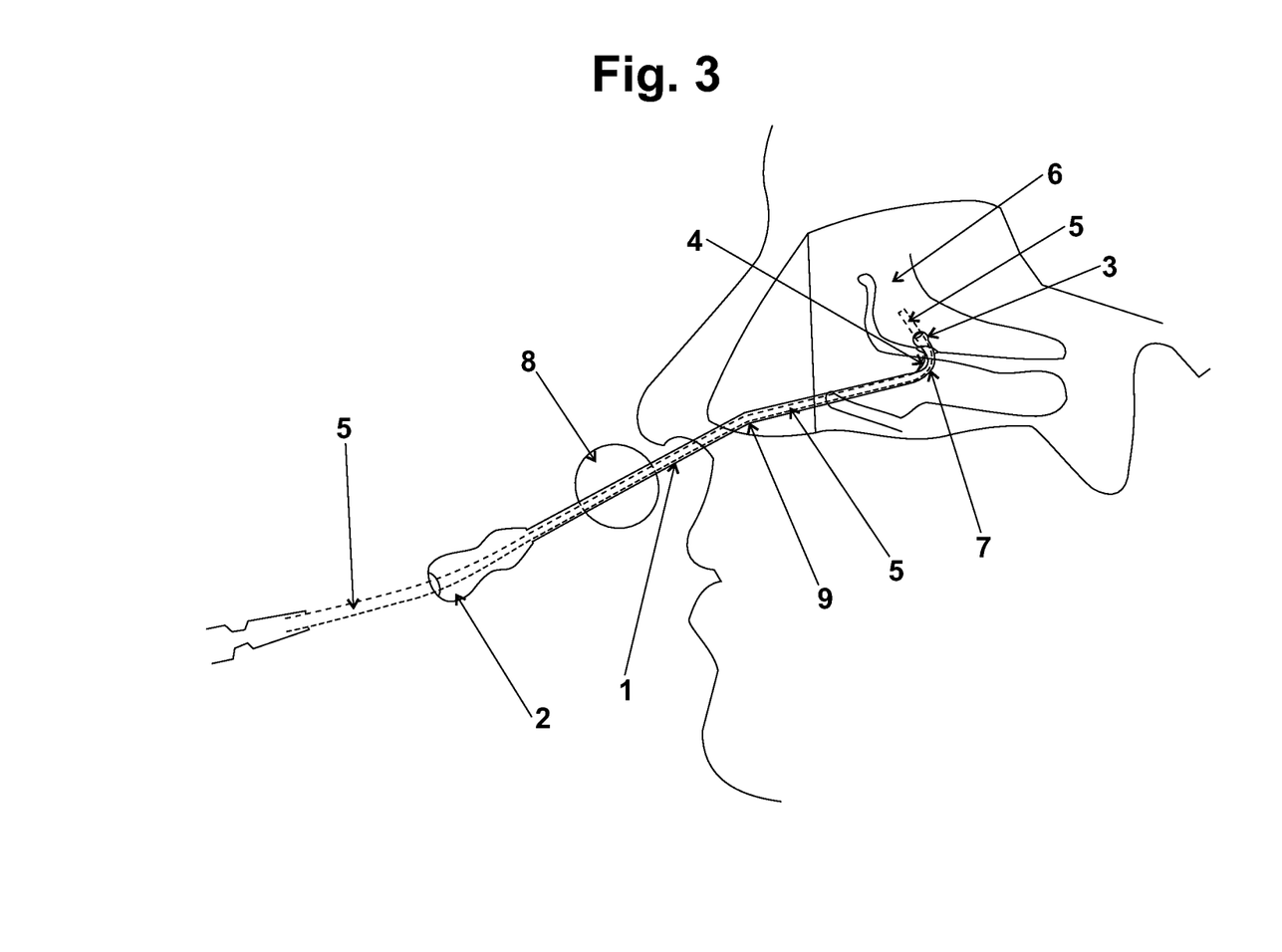
FIG. 3. shows an illustration of an embodiment of the cannula guide tube of the present invention, wherein the tube has inside a flexible transparent cannula, and wherein the tube end is in the orifice entrance of a human maxillary sinus and the flexible transparent cannula is inserted, by means of the tube, inside the maxillary sinus.
Figure 4:
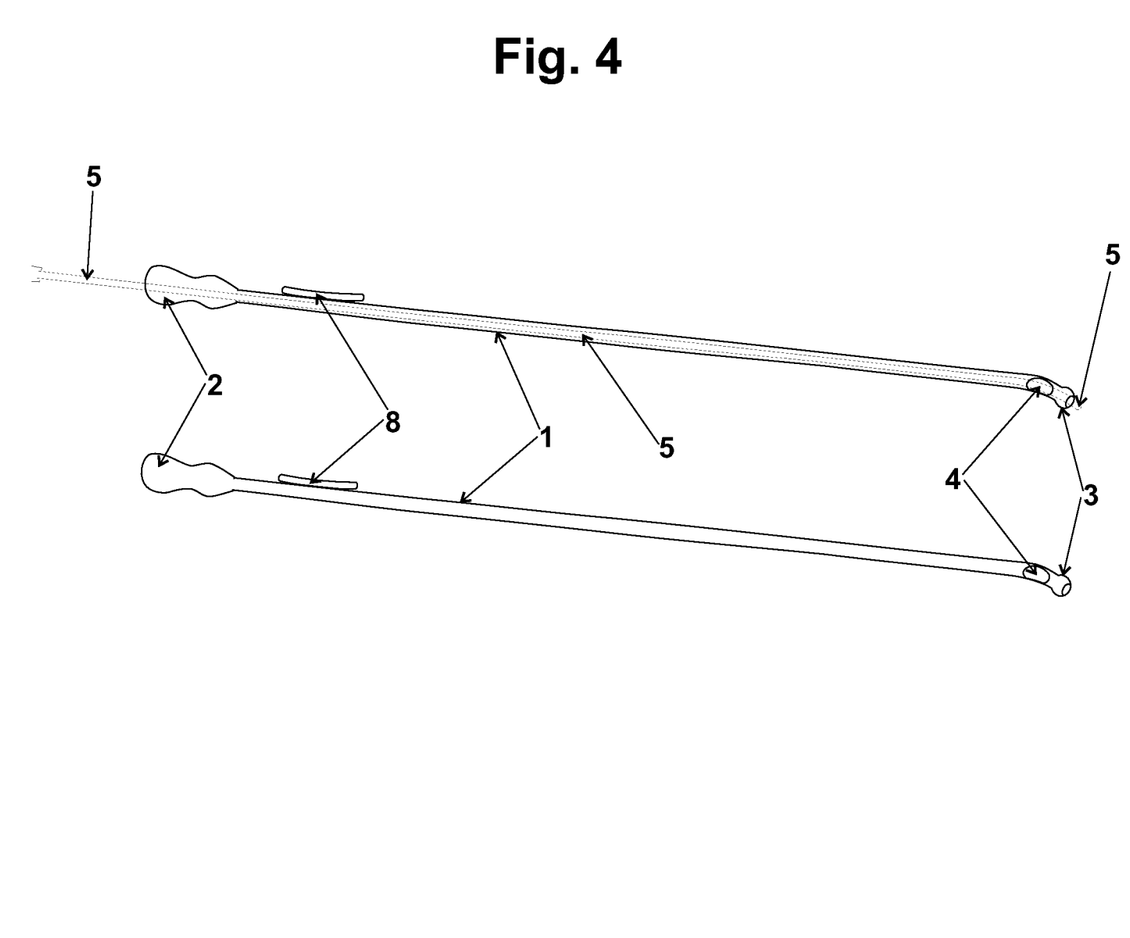
FIG. 4. shows an embodiment of the cannula guide tube of the present invention with and without the flexible transparent cannula inside the tube, and wherein the opening before the end of the tube is clearly shown.
Figure 5:
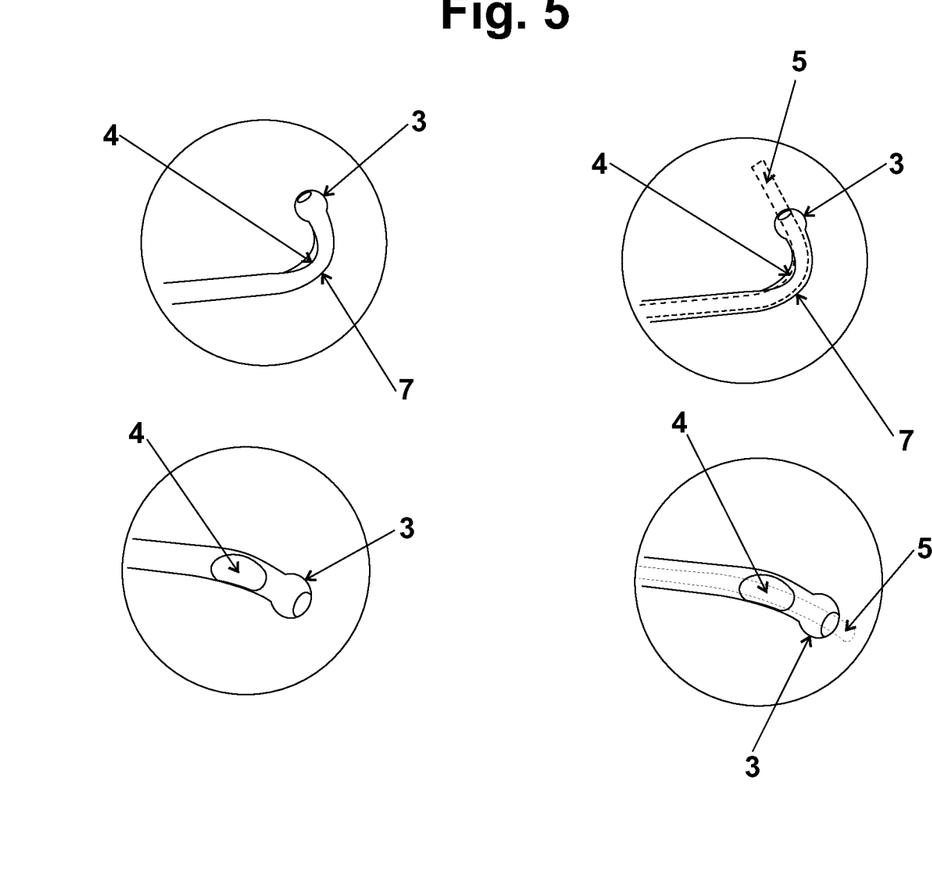
FIG. 5. shows amplifications of the cannula guide tube end of the present invention with and without the flexible transparent tube. These amplifications show clearly the opening before the end of the tube.

In a preferred aspect of the present invention, the cannula guide tube middle portion has a bend (9) (FIGS. 1 to 3). The bend will allow easier manipulation of the cannula guide tube in some situations. However, sometimes the cannula guide tube will be easier to manipulate if said bend is not present.

Figure 6:
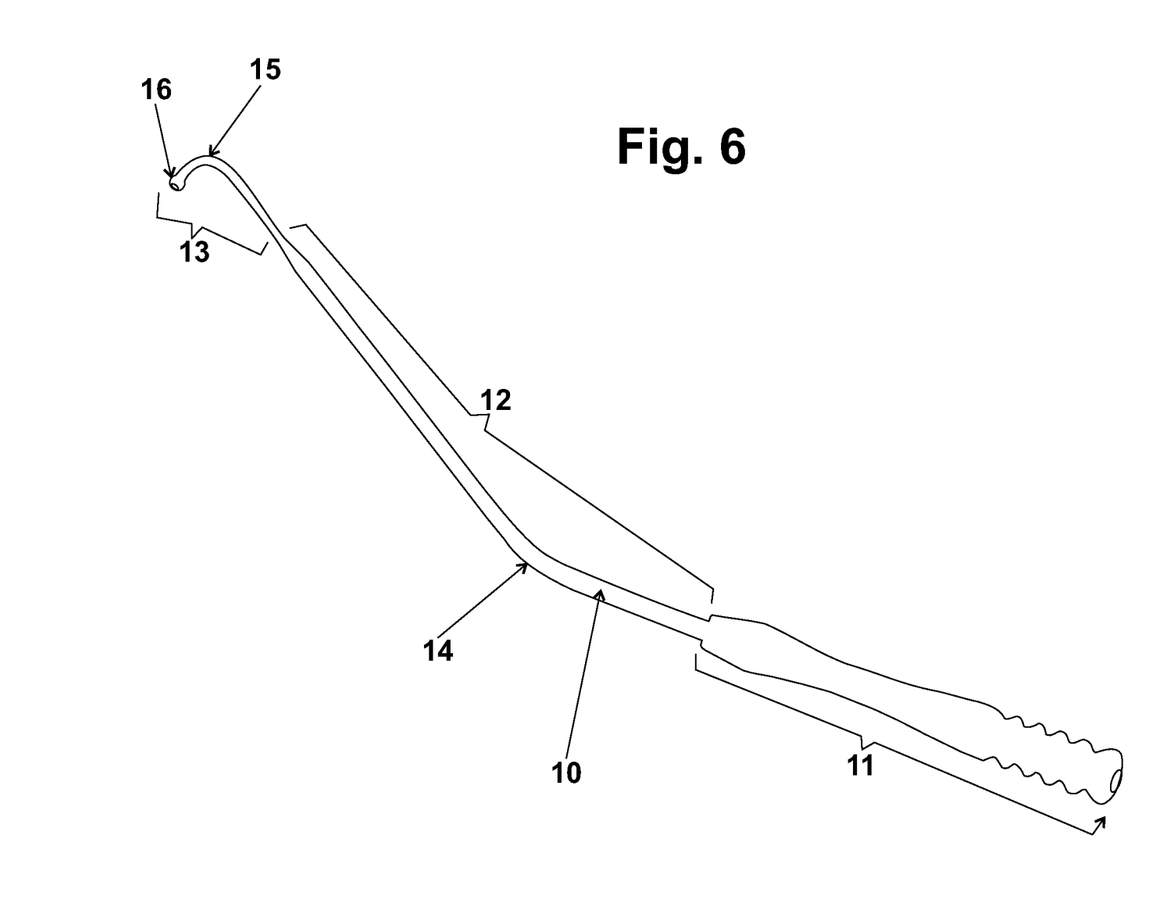
FIG. 6. shows the exploratory tubular device of the kit of the present invention.
Figure 7:
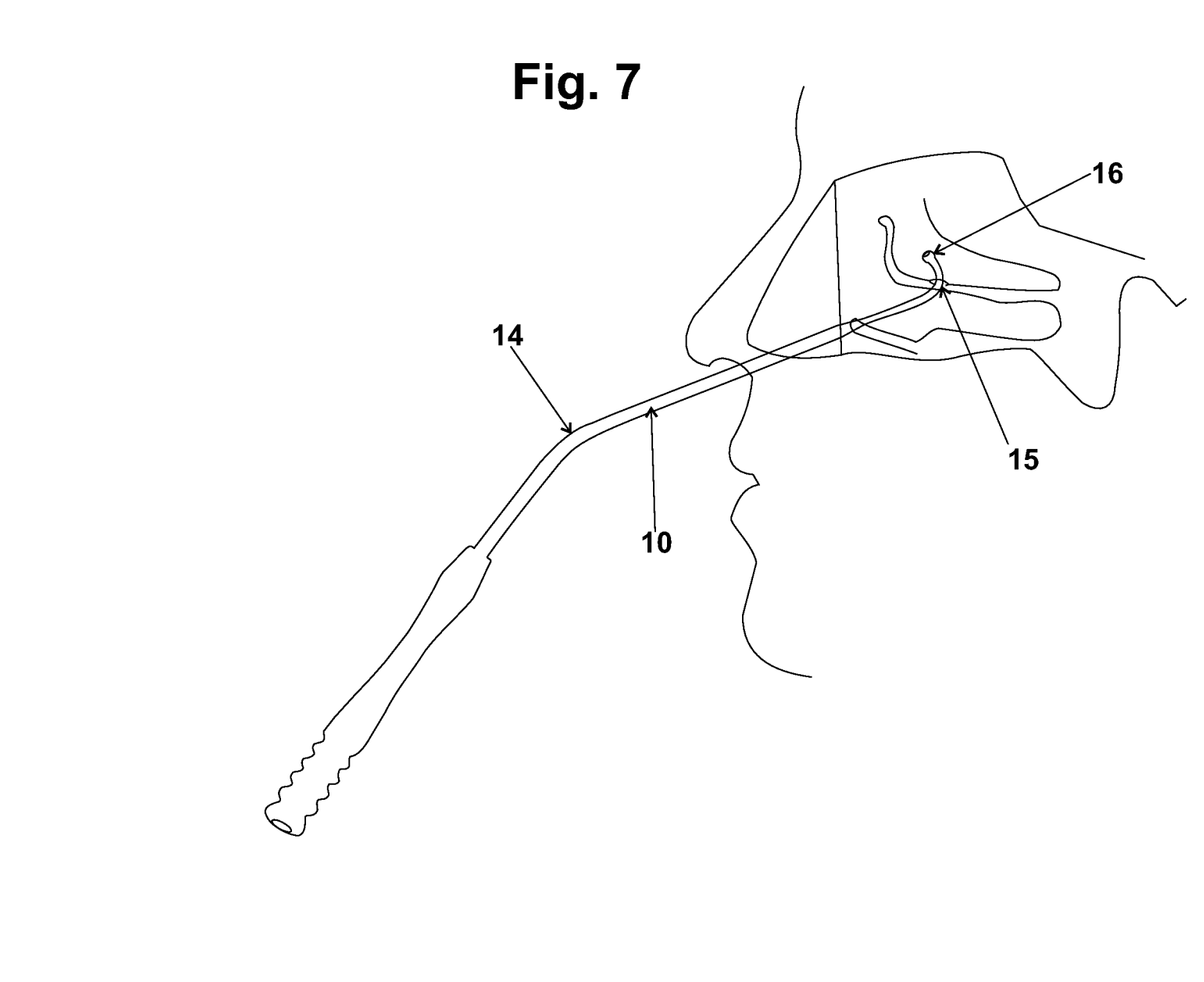
FIG. 7. shows the exploratory tubular device of the kit of the present invention, wherein the device is positioned at the orifice entrance of a human maxillary sinus.
Figure 8:
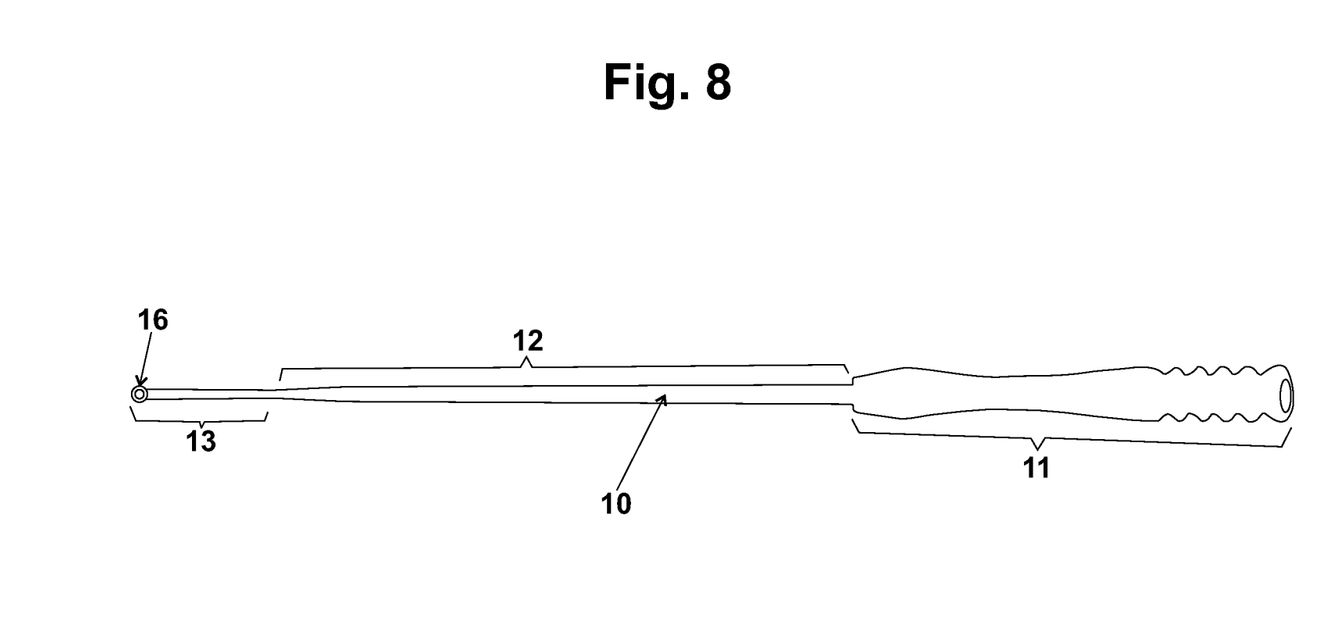
FIG. 8. shows another view of the exploratory tubular device of the kit of the present invention.

The present invention also provides a kit for irrigation, suction and washing out purulent discharges or liquids from a sinus, wherein the kit comprises:

A. a cannula guide tube (1) with a beginning (2) and an end (3), wherein the tube (1) has an opening (4) on the tube portion preceding the end (3); wherein the cannula guide tube (1) is used to conduct a flexible transparent cannula (5) or a transparent catheter with an inflatable balloon to a sinus cavity (6), wherein the flexible transparent cannula (5) or the transparent catheter is used for irrigation, suction and washing out purulent discharges or liquids from the sinus cavity, wherein the opening (4) allows to see the purulent discharge or liquid flow that is getting out from the sinus cavity, wherein the opening (4) also allows to see a clean washing fluid flow after the purulent discharge is clear out of the sinus cavity;

B. A flexible transparent cannula (4) or a transparent catheter with an inflatable balloon at the catheter termination;

C. An exploratory tubular device (FIGS. 6 to 8) (10) that has first portion (FIGS. 6 and 8) (11), a second portion (FIGS. 6 and 8) (12) and a third portion (FIGS. 6 and 8) (13), wherein the first portion (11) serves as the device holder, wherein the first portion (11) is the thickest portion, wherein the second portion (12) is the second uniformly thickest portion, wherein the third portion (13) is the least thick portion, wherein the third portion (13) termination is non-sharp.

In a preferred use of the kit of the present invention, the kit is used to drain out purulent discharges or liquids from human sinuses, e.g., maxillary sinuses. However, the kit of the present invention can be also used to drain out discharges or liquids from animal sinuses.

In addition, kit of the present invention can serve to irrigate other human or animal ducts, e.g., lachrymal ducts, wherein irrigating would clear blockages of said ducts.

In a preferred aspect of the kit of the present invention, the cannula guide tube end (3) forms an angle (7) with respect to the rest of the tube, wherein the opening (4) is inside of the angle (7) just before the tube end (3). However, there may be situations wherein the angle before the end is not necessary.

In another preferred aspect of the kit of the present invention, the cannula guide tube end (3) has a non-sharp rounded olive shape (3). However, the cannula guide tube end not necessarily has to have a olive shape finish, as long as, the cannula guide tube end does not have sharp borders that could damage soft tissues or inflammated tissues.

The cannula guide tube of the kit of the present invention preferably is made of stainless steel which will allow sterilization and reusing said cannula guide tube. However, the cannula guide tube of the present invention can also be made of any inert hard material, e.g., hard plastic, even if it is not reusable.

In one more aspect of the kit of the present invention, the cannula guide tube beginning (2) has a thickened pear like shape (2).

In an additional aspect of the kit of the present invention, the cannula guide tube (1) has attached a coin shaped disk (8) for gripping.

In a further aspect of the kit of the present invention, the cannula guide tube middle portion has a bend (9). The bend will allow easier manipulation of the cannula guide tube in some situations. However, sometimes the cannula guide tube will be easier to manipulate if said bend is not present.

In a preferred aspect of the kit of the present invention, the tubular device second portion (12) has a bend (14).

Figure 9:
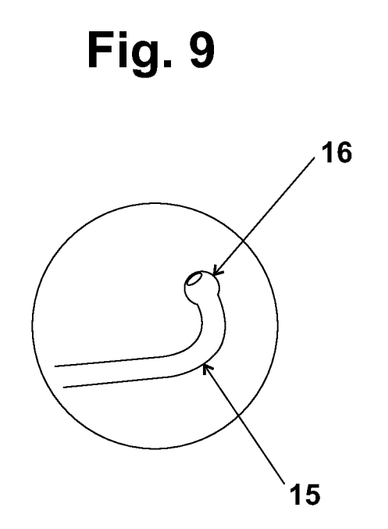
FIG. 9. shows an amplification of exploratory tubular device termination (third portion part) of the kit of the present invention.

In one extra preferred aspect of the kit of the present invention, the tubular device third portion (13) termination forms an angle (FIGS. 6, 7, and 9) (15) with respect to the rest of the tubular device.

In one more aspect of the kit of the present invention, the tubular device third portion termination (FIGS. 6 to 9) (16) has a non-sharp olive shape (16). However, the tubular device third portion termination not necessarily has to have a olive shape, as long as, tubular device third portion termination does not have sharp borders that could damage soft tissues or inflammated tissues.

Objectives and advantages of the present Application invention will be more evident in the detailed description of the invention and the claims.

The invention claimed is:

1. A kit for irrigation, suction and washing out purulent sinusitis discharges, wherein the kit comprises:
   A. a cannula guide tube with a beginning and an end, wherein the tube has an opening on the tube portion preceding the end, wherein the opening is a hole on the wall of the tube, wherein the opening does not extend to the end of the tube, wherein the end of the tube does not have sharp borders; wherein the cannula guide tube is used to conduct a flexible transparent cannula to a sinus cavity, wherein the flexible transparent cannula is used for irrigation, suction and washing out purulent discharges from the sinus cavity, wherein the opening allows to see the purulent discharge flow that is getting out from the sinus cavity, wherein the opening also allows to see a clean washing fluid flow after the purulent discharge is clear out of the sinus cavity;
   B. A flexible transparent cannula;
   C. An exploratory tubular device that has first portion, a second portion and a third portion, wherein the first portion serves as the device holder, wherein the first portion is the thickest portion, wherein the second portion is the second uniformly thickest portion, wherein the third portion is the least thick portion, wherein the third portion termination is non-sharp.

2. The kit of claim 1, wherein the cannula guide tube end forms an angle with respect to the rest of the tube, wherein the opening is inside of the angle just before the tube end.

3. The kit of claim 1, wherein the cannula guide tube end has a non-sharp rounded olive shape.

4. The kit of claim 1, wherein the cannula guide tube beginning has a thickened pear like shape.

5. The kit of claim 1, wherein the cannula guide tube has attached a coin shaped disk for gripping.

6. The kit of claim 1, wherein the cannula guide tube middle portion has a bend.

7. The kit of claim 1, wherein the transparent flexible cannula is a transparent catheter with an inflatable balloon at the catheter termination.

8. The kit of claim 1, wherein the tubular device second portion has a bend.

9. The kit of claim 1, wherein the tubular device third portion termination forms an angle with respect to the rest of the tubular device.

10. The kit of claim 1, wherein the tubular device third portion termination has a non-sharp olive shape.

* * * * *